(12) United States Patent
Zamani et al.

(10) Patent No.: US 8,409,290 B2
(45) Date of Patent: Apr. 2, 2013

(54) INTERBODY DEVICE FOR SPINAL APPLICATIONS

(75) Inventors: Shahram Shaun Zamani, San Diego, CA (US); Nicholas M. Cordaro, Vista, CA (US); Colin M. Smith, Dana Point, CA (US)

(73) Assignee: SeaSpine, Inc., Vista, CA (US)

( * ) Notice: Subject to any disclaimer, the term of this patent is extended or adjusted under 35 U.S.C. 154(b) by 344 days.

(21) Appl. No.: 12/753,759

(22) Filed: Apr. 2, 2010

(65) Prior Publication Data

US 2010/0191337 A1 Jul. 29, 2010

Related U.S. Application Data

(63) Continuation-in-part of application No. 11/371,539, filed on Mar. 8, 2006, now abandoned, and a continuation-in-part of application No. 11/919,615, filed on Oct. 30, 2007, now Pat. No. 7,799,083, and a continuation-in-part of application No. 11/919,616, filed on Oct. 30, 2007, now Pat. No. 8,097,036.

(51) Int. Cl.
*A61F 2/44* (2006.01)
(52) U.S. Cl. .................................................. 623/17.16
(58) Field of Classification Search ..... 623/17.11–17.16
See application file for complete search history.

(56) References Cited

U.S. PATENT DOCUMENTS

| | | |
|---|---|---|
| 5,071,437 A | 12/1991 | Steffee |
| 5,431,658 A | 7/1995 | Moskovich |
| 5,676,701 A | 10/1997 | Yuan |
| 5,733,290 A | 3/1998 | McCue et al. |
| 5,755,796 A | 5/1998 | Ibo et al. |
| 5,888,222 A | 3/1999 | Coates et al. |
| 5,899,941 A | 5/1999 | Nishijima et al. |
| 6,033,438 A | 3/2000 | Bianchi et al. |
| 6,113,637 A | 9/2000 | Gill et al. |
| 6,113,638 A | 9/2000 | Williams et al. |
| 6,193,757 B1 | 2/2001 | Foley et al. |
| 6,206,924 B1 | 3/2001 | Timm |
| 6,235,059 B1 | 5/2001 | Benezech et al. |
| 6,258,125 B1 | 7/2001 | Paul et al. |
| 6,319,257 B1 | 11/2001 | Carignan et al. |
| 6,368,350 B1 | 4/2002 | Erickson et al. |
| 6,368,354 B2 | 4/2002 | Burstein et al. |
| 6,423,095 B1 | 7/2002 | Van Hoeck et al. |
| 6,478,801 B1 | 11/2002 | Ralph et al. |
| 6,482,233 B1 | 11/2002 | Aebi et al. |
| 6,520,993 B2 | 2/2003 | James et al. |
| 6,572,619 B2 | 6/2003 | Santilli |
| 6,579,318 B2 | 6/2003 | Varga et al. |
| 6,595,998 B2 | 7/2003 | Johnson et al. |
| 6,635,086 B2 | 10/2003 | Lin |
| 6,673,075 B2 | 1/2004 | Santilli |
| 6,699,288 B2 | 3/2004 | Moret |

(Continued)

FOREIGN PATENT DOCUMENTS

| | | |
|---|---|---|
| DE | 2263842 | 12/1972 |
| WO | WO-2004/000177 A1 | 12/2003 |

OTHER PUBLICATIONS

International Search Report and Written Opinion dated Jun. 21, 2011 for PCT/US2011/030984 in 11 pages.

(Continued)

*Primary Examiner* — Sameh Boles
(74) *Attorney, Agent, or Firm* — James W. Hill; McDermott Will & Emery LLP

(57) ABSTRACT

An intervertebral spacer includes a leading end, a trailing end comprising an opening having a clearance and a post positioned across the clearance. The post has an external surface configured to accept an extending portion of an insertion tool and to torsionally engage a complementary surface of the insertion tool at a plurality of different angles.

10 Claims, 7 Drawing Sheets

U.S. PATENT DOCUMENTS

| | | |
|---|---|---|
| 6,706,068 B2 | 3/2004 | Ferree |
| 6,719,794 B2 | 4/2004 | Gerber et al. |
| 6,736,849 B2 | 5/2004 | Li et al. |
| 6,743,257 B2 | 6/2004 | Castro |
| D493,225 S | 7/2004 | Varga et al. |
| 6,758,862 B2 | 7/2004 | Berry et al. |
| D494,274 S | 8/2004 | Varga et al. |
| 6,793,678 B2 | 9/2004 | Hawkins |
| RE38,614 E | 10/2004 | Paul et al. |
| 6,800,092 B1 | 10/2004 | Williams et al. |
| 6,805,714 B2 | 10/2004 | Sutcliffe |
| D501,555 S | 2/2005 | Varga et al. |
| 6,890,355 B2 | 5/2005 | Michelson |
| 6,899,735 B2 | 5/2005 | Coates et al. |
| 6,964,686 B2 | 11/2005 | Gordon |
| 6,966,929 B2 | 11/2005 | Mitchell |
| 6,966,932 B1 | 11/2005 | Schroeder |
| 6,974,480 B2 | 12/2005 | Messerli et al. |
| 7,048,764 B2 | 5/2006 | Ferree |
| 7,060,073 B2 | 6/2006 | Frey et al. |
| 7,105,023 B2 | 9/2006 | Eckman |
| D533,277 S | 12/2006 | Blain |
| 7,156,876 B2 | 1/2007 | Moumene et al. |
| 7,198,643 B2 | 4/2007 | Zubok et al. |
| 7,217,293 B2 | 5/2007 | Branch, Jr. |
| 7,229,477 B2 | 6/2007 | Biscup |
| 7,235,101 B2 | 6/2007 | Berry et al. |
| 7,250,060 B2 | 7/2007 | Trieu |
| 7,276,082 B2 | 10/2007 | Zdeblick et al. |
| RE40,260 E | 4/2008 | Buhler |
| D566,276 S | 4/2008 | Blain |
| 7,470,273 B2 | 12/2008 | Dougherty-Shah |
| D585,553 S | 1/2009 | Valois |
| 7,476,252 B2 | 1/2009 | Foley |
| 7,500,991 B2 | 3/2009 | Bartish, Jr. et al. |
| 7,503,933 B2 | 3/2009 | Michelson |
| 7,517,363 B2 | 4/2009 | Rogers et al. |
| 7,537,612 B2 | 5/2009 | Kunzler |
| 7,563,284 B2 | 7/2009 | Coppes et al. |
| 7,575,580 B2 | 8/2009 | Lim et al. |
| D620,113 S | 7/2010 | Courtney et al. |
| 7,806,932 B2 | 10/2010 | Webb et al. |
| 7,815,682 B1 | 10/2010 | Peterson et al. |
| D629,108 S | 12/2010 | Richter et al. |
| D630,749 S | 1/2011 | Tornier |
| 7,892,239 B2 | 2/2011 | Warnick et al. |
| 7,901,458 B2 | 3/2011 | DeRidder et al. |
| 7,938,857 B2 | 5/2011 | Garcia-Bengochea et al. |
| 7,959,675 B2 | 6/2011 | Gately |
| 7,976,549 B2 | 7/2011 | Dye et al. |
| 7,988,695 B2 | 8/2011 | Dye |
| 7,998,212 B2 | 8/2011 | Schwab et al. |
| 8,021,429 B2 | 9/2011 | Viker |
| 8,025,684 B2 | 9/2011 | Garcia-Bengochea et al. |
| 8,034,110 B2 | 10/2011 | Garner et al. |
| 8,043,293 B2 | 10/2011 | Warnick |
| 8,137,404 B2 | 3/2012 | Lopez et al. |
| 8,147,554 B2 | 4/2012 | Hansell et al. |
| 8,157,845 B2 | 4/2012 | Warnick et al. |
| 2001/0020170 A1 | 9/2001 | Zucherman et al. |
| 2003/0045939 A1 | 3/2003 | Casutt |
| 2003/0069586 A1 | 4/2003 | Errico et al. |
| 2003/0100950 A1 | 5/2003 | Moret |
| 2004/0097929 A1 | 5/2004 | Branch et al. |
| 2004/0167538 A1 | 8/2004 | Gerber et al. |
| 2004/0243241 A1 | 12/2004 | Istephanous et al. |
| 2005/0027360 A1 | 2/2005 | Webb et al. |
| 2005/0038431 A1 | 2/2005 | Bartish et al. |
| 2005/0038516 A1 | 2/2005 | Spoonamore |
| 2005/0071005 A1 | 3/2005 | Carli et al. |
| 2005/0096745 A1 | 5/2005 | Andre et al. |
| 2005/0143822 A1 | 6/2005 | Paul |
| 2006/0149273 A1 | 7/2006 | Ross et al. |
| 2006/0229627 A1 | 10/2006 | Hunt |
| 2006/0229729 A1 | 10/2006 | Gordon et al. |
| 2007/0093897 A1 | 4/2007 | Gerbec et al. |
| 2007/0162128 A1 | 7/2007 | DeRidder et al. |
| 2007/0162138 A1 | 7/2007 | Heinz |
| 2007/0213826 A1 | 9/2007 | Smith et al. |
| 2007/0225808 A1 | 9/2007 | Warnick |
| 2007/0282449 A1 | 12/2007 | de Villiers et al. |
| 2008/0009880 A1 | 1/2008 | Warnick et al. |
| 2008/0051890 A1 | 2/2008 | Waugh et al. |
| 2008/0077153 A1 | 3/2008 | Pernsteiner et al. |
| 2008/0077247 A1 * | 3/2008 | Murillo et al. ............. 623/17.16 |
| 2008/0275506 A1 | 11/2008 | Baynham et al. |
| 2009/0054991 A1 | 2/2009 | Biyani et al. |
| 2009/0082868 A1 | 3/2009 | Cordaro et al. |
| 2009/0143859 A1 | 6/2009 | McClellan, III et al. |
| 2009/0248163 A1 | 10/2009 | King et al. |
| 2009/0276049 A1 | 11/2009 | Weiland |
| 2010/0030270 A1 | 2/2010 | Winslow et al. |
| 2010/0121455 A1 | 5/2010 | Lambrecht et al. |
| 2010/0185292 A1 | 7/2010 | Hochschuler et al. |
| 2010/0191337 A1 | 7/2010 | Zamani et al. |
| 2010/0217395 A1 | 8/2010 | Bertagnoli et al. |
| 2010/0305706 A1 | 12/2010 | Webb et al. |

OTHER PUBLICATIONS

Official Action—dated Aug. 10, 2011 in copending U.S. Appl. No. 11/371,539 in 11 pages.

Official Action dated Apr. 30, 2008, co-pending U.S. Appl. No. 11/371,453.

Hoffman-Daimler, Intervertebral Disk Displacement, vol. 112, No. 4, Aug. 1974.

Trouillier, H. et al., "Report on Two Failed Posterior Lumbar Interbody Fusions", SICOT Online Report E034: Accepted May 6, 2003, Department of Orthopedic Surgery, Institute of Pathology, Ludwig-Maximilians University, Munich, Germany, pp. 1-12.

\* cited by examiner

INTERBODY DEVICE FOR SPINAL APPLICATIONS

CROSS REFERENCE TO RELATED APPLICATIONS

The present application is a continuation-in-part of (i) U.S. application Ser. No. 11/371,539, filed on Mar. 8, 2006, (ii) U.S. application Ser. No. 11/919,615, which entered the national stage under 35 U.S.C. §371 on Oct. 30, 2007, of PCT/US2006/016392, filed on Apr. 28, 2006, and now issued as U.S. Pat. No. 7,799,083, and (iii) U.S. application Ser. No. 11/919,616, which entered the national stage under 35 U.S.C. §371 on Oct. 30, 2007, of PCT/US2006/016399, filed on Apr. 28, 2006, and now issued as U.S. Pat. No. 8,097,036, the entire contents of each of which are incorporated herein by reference.

FIELD

The present disclosure relates, in general, to artificial prosthetics, and more particularly, to intervertebral spacers.

BACKGROUND

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the annulus to buckle in areas where the laminated plies are loosely bonded. As the overlapping laminated plies of the annulus begin to buckle and separate, either circumferential or radial annular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases it is desired to fuse the adjacent vertebrae together after removal of the disc, sometimes referred to as "intervertebral fusion" or "interbody fusion."

In cases of intervertebral fusion, it is known to position a spacer centrally within the space where the spinal disc once resided, or to position multiple spacers within that space. Such practices are characterized by certain disadvantages, including a disruption in the natural curvature of the spine. For example, the vertebrae in the lower "lumbar" region of the spine reside in an arch referred to in the medical field as having a sagittal alignment. The sagittal alignment is compromised when adjacent vertebral bodies that were once angled toward each other on their posterior side become fused in a different, less angled orientation relative to one another.

While the occurrence of successful spinal surgeries of any of the variety mentioned above has greatly improved in recent years, there continue to be challenges and room for improvement in the area of intervertebral spacers and prosthetics. In particular, a patient's precise anatomy is often not known prior to surgery although general predictions will be available. Additionally, while surgery is a well-planned process, not all conditions can be known beforehand and some variations will likely not be ideal. Accordingly, during surgery a surgeon will likely need to make decisions that balance speed, safety, and efficacy. One such decision can relate to the approach angle at which the spacer is inserted into the patient's body. This angle can vary either anteriorally or posteriorally from a lateral approach depending on the surgical conditions encountered. A spacer that is adaptable to the wide vagaries of surgical conditions that might be encountered will provide many benefits to patients and surgeons. Presently, many intervertebral spacers require an insertion tool that fixedly threads into the spacer's body thereby limiting the alignment between the tool and the spacer to a single position. Thus, there remains a need for intervertebral spacers that offer the surgeon more ease-of-use and flexibility than the spacers that are currently available.

U.S. Patent Pub. No. 2008/0009880 and U.S. Patent Pub. No. 2008/0221694 A1 disclose a spinal spacer system that includes a proximal end, a distal end, and a rotatably couplable engagement member disposed on the proximal end. The inserter extends around a transverse feature and the spacer is able to rotate freely relative to the inserter. However, pivoting is performed on the engagement member, requiring accurate angular orientation and manipulation of the engagement member by a surgeon during the placement of a spacer.

There remains a need for intervertebral spacers that offer the surgeon more ease-of-use and flexibility than the spacers that are currently available.

SUMMARY

The above discussed and other needs are fulfilled by interbody devices such as intervertebrate spacers according to various configurations described in the present disclosure.

In one aspect of the present disclosure, an intervertebral spacer including a leading end, a trailing end comprising an opening having a clearance and a post positioned across the clearance are disclosed. The post has an external surface configured to accept an extending portion of an insertion tool and to torsionally engage a complementary surface of the insertion tool at a plurality of different angles.

In another aspect of the present disclosure, an intervertebral spacer is disclosed. The spacer includes a leading end. The spacer further includes a trailing end comprising an opening. The spacer further includes a substantially planar superior side extending substantially from the leading end to the trailing end and having a superior side recess. The spacer further includes a substantially planar inferior side, opposite and parallel to the superior side, extending substantially from the leading end to the trailing end, and having an inferior side recess. An outside surface of the superior side and an outside surface of the inferior side comprise tooth patterns. Each tooth pattern comprises a plurality of teeth extending lengthwise between the anterior side and the posterior side. Teeth between a midpoint and the trailing end are angled with respect to a minor axis of the spacer towards the leading end and teeth between the midpoint and the leading end are angled with respect to the minor axis of the spacer towards the trailing edge.

In yet another aspect of the disclosure, an intervertebral spacer includes a leading end and a trailing end comprising an opening. The spacer further includes an arcuate anterior side connecting the leading end and the trailing end. The spacer further includes an arcuate posterior side opposite to the arcuate anterior side and connecting the leading end and the trailing end and having radius of curvature different from that of the arcuate anterior side. The spacer further includes a major axis extending from the leading end to the trailing end of the spacer and an interdigitation feature on an outside surface of the posterior side, the interdigitation feature oriented lengthwise in a direction perpendicular to the major axis.

In yet another aspect of the disclosure, an intervertebral spacer includes a leading end, a trailing end comprising an opening, a superior side connecting the leading end and the trailing end and having a superior side recess at the trailing end, an inferior side opposite to the anterior side and connecting the leading end and the trailing end and having an inferior side recess at the trailing end, a post extending between the superior side recess and the inferior side recess and configured to accept a sleeve around the post, and a sleeve around the post, extending substantially between the superior side recess and the inferior side recess, the sleeve configured to rotate about the post and having an external surface configured to accept an extending portion of an insertion tool and to torsionally engage a complementary surface of the insertion tool at a plurality of different angles.

The foregoing and other features, aspects and advantages of the embodiments of the present disclosure will become more apparent from the following detailed description and accompanying drawings.

DETAILED DESCRIPTION

The detailed description set forth below in connection with the appended drawings is intended as a description of various embodiments of the disclosure and is not intended to represent the only embodiments in which the invention may be practiced. The detailed description includes specific details for the purpose of providing a thorough understanding of the disclosure. However, it will be apparent to those skilled in the art that the invention may be practiced without these specific details. In some instances, well known structures and components are shown in block diagram form in order to avoid obscuring the concepts of the disclosure.

Figure 1:
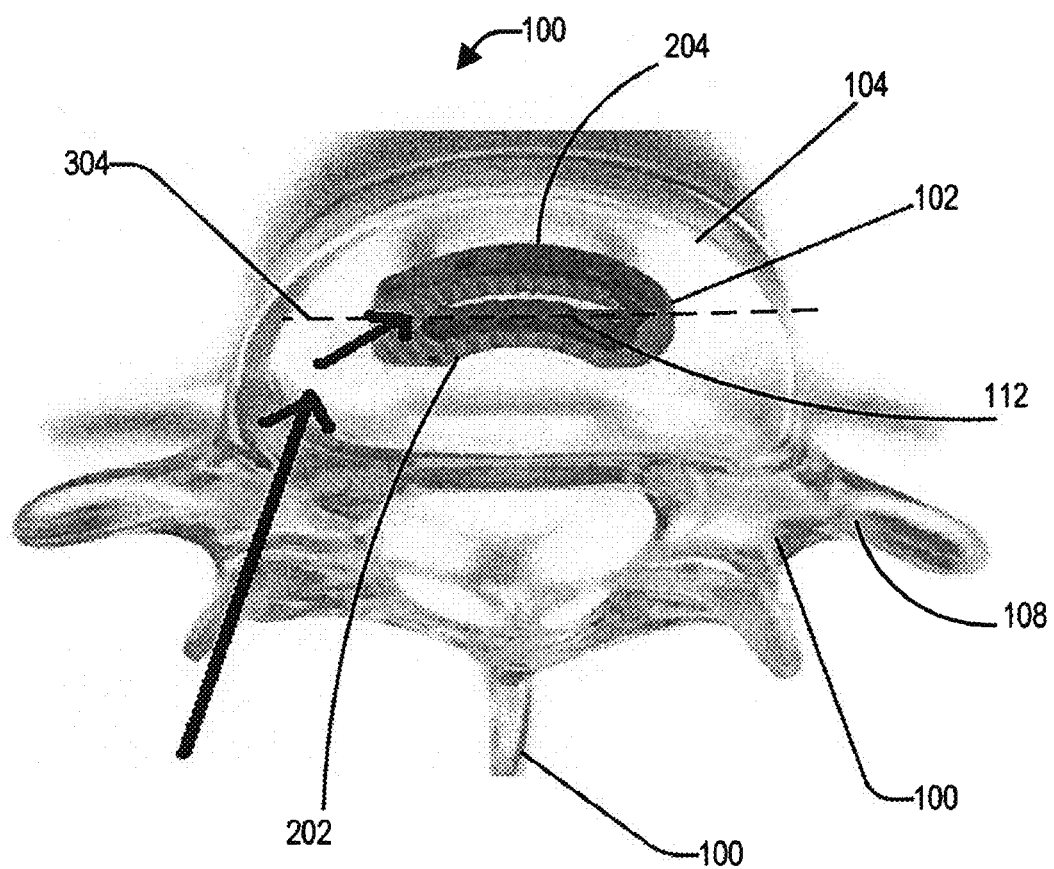
FIG. 1 is a diagrammatic representation of an intervertebral spacer arranged on a vertebrate body in accordance with certain embodiments of the present application.

FIG. 1 illustrates one typical environment in which intervertebral spacers may be used in accordance with the principles of the present disclosure. The spacer 102 is shown on top of a vertebrae body 104. The spinous process 106 is located posteriorally with respect to the body 104. The transverse process 108 and the lamina 110 are located between the body 104 and the spinous process 106. The second vertebrae body positioned over top of the spacer 102 is not shown in FIG. 1 for purposes of clarity. However, as is well known to one of ordinary skill, the spacer 102 is used in this manner to separate two adjacent vertebrae bodies.

The spacer 102 of FIG. 1 is generally kidney-shaped and includes contours that roughly follow the shape of the vertebrae body 104. In certain configurations, spacer 102 is rectangular in shape. For purposes of orientation, the posterior portion 202 of the spacer 102 is located closer to the spinous process 106 and the anterior portion 204 is located away from the spinous process 106. This orientation is for purposes of providing a consistent frame of reference and is not intended to be interpreted as a limitation of the present disclosure.

The spacer 102 may be used in a variety of configurations; however, the configuration of FIG. 1 is a typical configuration with the spacer 102 located near the anterior region of the vertebrae body 104. During surgery, a surgeon will place the spacer 102 at this location and may do so using a variety of techniques. In particular, the arrow 112 indicates a direction generally referred to, with respect to spacer implants, as transforaminal. This arrow 112 indicates the general direction in which the spacer 102 is inserted between two adjacent vertebrae bodies. Advantageous attributes of the present disclosure allow this direction 112 to widely vary, even during surgery, to allow a surgeon great flexibility in inserting the spacer 102. Furthermore, the orientation of the major axis 304 of the spacer 102 relative to the direction 112 may vary as well.

Because the spacer 102 is designed for insertion in a patient's body, its material is selected to withstand such an environment without deteriorating or harming the patient. Exemplary materials useful in this environment include, but are not limited to, polyether ether ketone, titanium, artificial bone material, and natural bone tissue. Other similar material may be used without departing from the scope of the present disclosure.

FIGS. 2 to 8 show different views of more detailed depictions of various embodiments of the spacer 102. A number of the features described with reference to these figures are optional but provide certain advantages. For example, holes may be present that permit the insertion of bone-grafting material that helps fuse the spacer to adjacent spinal bodies. Also, the spacer surfaces which are adjacent vertebrae bodies may be rough, or otherwise "keyed", to improve the mechanical adherence of the spacer to the bodies. In this way, the spacer is less likely to move or shift once it has been surgically implanted.

Figure 2:
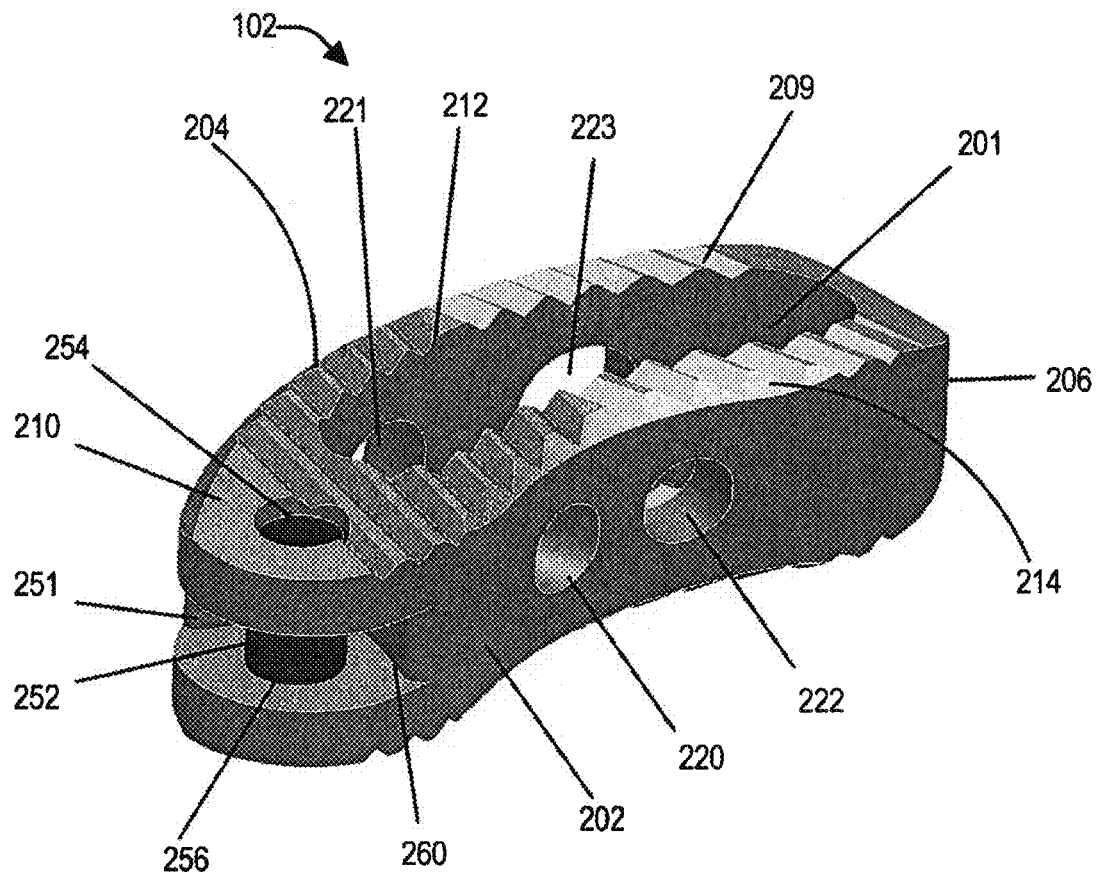
FIG. 2 is a diagrammatic representation of an intervertebral spacer, in accordance with certain embodiments of the present application.
Figure 3:
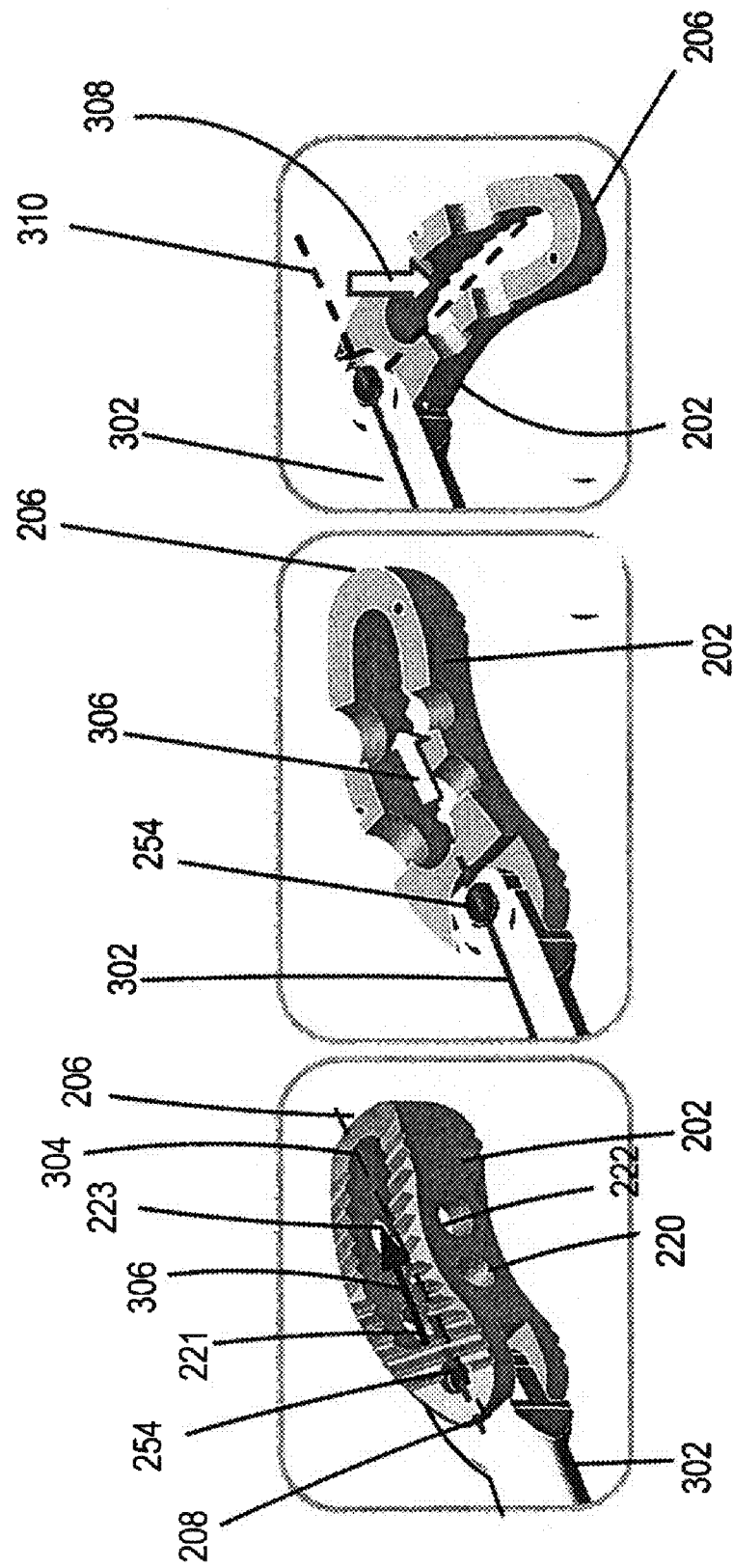
FIG. 3A to 3C are diagrammatic representations of coupling of an intervertebral spacer with an insertion tool, in accordance with certain configurations of the present application.

FIG. 2 depicts a diagrammatic view of the spacer 102 in which the leading end 206 and the trailing end 208 are visible. The trailing end 208 has an opening 251 in which the post 252 is positioned. The post 252 extends across the clearance of the opening 251. The external surface of the post 252 is configured to accept an extending portion of an insertion tool (not shown in FIG. 2) to torsionally engage a complementary surface of the insertion tool at a plurality of different angles, as will be further described in details.

The post 252 provides an interface with an inserter (not shown in FIG. 2) that enables the spacer 102 to rotate while being inserted into the intervertebral space. During insertion, a surgeon can advantageously use the torsional engagement between the inserter and the post 252 to move the spacer 102 back and forth in the insertion direction and also angle the spacer 102 as needed. In certain embodiments, the surgeon is able to control the amount of torsional coupling between the inserter and the post 252 by selectively torsionally engaging the inserter with the post 252.

Still referring to FIG. 2, the spacer 102 can be seen as a kidney-shaped cage having an internal cavity 201. As mentioned previously, this internal cavity 201 may be filled with bone-grafting material if desired. The spacer 102 includes an anterior side 204 connecting the leading end 206 and the trailing end 208. The spacer 102 further includes a posterior side 202 opposite to the anterior side 204 and connecting the leading end 206 to the trailing end 208.

As depicted in FIG. 2, the posterior side 202 and the anterior side 204 are arcuate and the spacer 102 is substantially kidney-shaped. In general, the posterior side 202 and the anterior side 204 have different respective radii of curvature, although they may have the same radius in certain embodiments.

Still referring to FIG. 2, the substantially planar superior side 209 is substantially perpendicular to the posterior and the anterior sides 202, 204 and extends from the leading end 206 to the trailing end 208. The substantially planar inferior side 211 is opposite to the superior side 209 and is also substantially perpendicular to the posterior and the anterior sides 202, 204 and extends from the leading end 206 to the trailing end 208.

Still referring to FIG. 2, the superior side 209 comprises teeth 212, 214. Teeth 212, 214 on the outside surfaces of the superior side 209 and the inferior side 211 are exemplary in nature and can vary in numerous ways, or even be absent, without departing from the scope of the present disclosure. For example, teeth 212, 214 may be pointed at their peaks (in cross-section) and have rounded, pointed, or squared valleys between adjacent peaks. The slope of the sides of the teeth 212, 214 may vary as well as the spacing between the teeth 212, 214. Similarly, the height of the teeth 212, 214 may vary as well. Because the posterior side 202 and anterior side 204 may be arcuate shaped, the teeth 212, 214 may be spaced variably such that they are closer at their posterior side end that at their anterior side end.

Still referring to FIG. 2, the post 252 is attached to the superior side 209 within a superior-side recess 254 and to the inferior side 211 within an inferior-side recess 256. In certain embodiments, such as depicted in FIG. 2, the recesses 254, 256 may be in the form of one or more through holes in the superior side 209 and the inferior side 211, wherein the post 252 is fitted. In certain other embodiments, recesses 254, 256 may be present on the interior surfaces of the superior side 209 and the inferior side 211 wherein the post 252 is fitted. In certain embodiments, the recesses 254, 256 are positioned at the trailing end 208, offset from the opening 251 in the direction of the leading end 206. The offsetting helps secure movement of the spacer 102 using an external tool (not shown in FIG. 2).

In certain embodiments, the post 252 is made of a polymeric material or a metallic material that can additionally be used as an X-ray marker. The metallic post 252 will further serve as a removal engagement point for the spacer 102 if need be due to higher strength than the other portions of the spacer 102. The spacer 102 may also include features that improve ease of insertion, osseointegration with osseoconduction and surface interdigitations for improved mechanical interlocking to the fusion mass. The post 252 can be press-fitted, threaded or attached by other means into the body. In certain embodiments, the post 252 provides structural strength to the spacer 102.

The outside surface of the post 252 is shaped to complement a corresponding gripping surface of an external inserting tool. For example, in various embodiments, the post 252 may be cylindrical in shape, or may have a hexagonal or rectangular outside surface to facilitate a firm grip with an external inserting tool.

Still referring to FIG. 2, the trailing end 208 includes an exterior surface 210 that has a tapering shape with an opening 251 to enable insertion of an external insertion tool to hold the post 252 during operation. The opening 251 extends between the superior side 209 and the inferior side 211 to be wide enough to allow the insertion tool to be inserted. Furthermore, the opening 251 extends between the posterior side 202 and the anterior side 212 to allow rotation of the insertion tool in its inserted position, as will be described in more detail later.

Still referring to FIG. 2, holes 220, 222 in the posterior side 202 and holes 221, 223 in the anterior side 204 are useful in providing access for bone-grafting material or other substances to be injected into the spacer 102 or may allow for vascularization after implant.

FIGS. 3A to 3C depict views in which an external inserter 302 is coupled to the post 252. In various embodiments, the shape of the surface of the post 252 conforms with the gripping surface of the inserter 302. For example, in various embodiments, the surface of the post 252 is circular, hexagonal or square and so on.

FIG. 3A depicts the external inserter 302 engaged in the engaging mechanism of the spacer (e.g., post 252). In the depicted embodiment, the external inserter 302 is generally aligned with the major axis 304 of the spacer 102 extending from the trailing end 208 to the leading end 206. During the operation of insertion of the spacer 102, such an alignment of the external inserter 302 with the major axis 304 of the spacer 102 enables a surgeon to insert the spacer 102 into an intervertebral gap at a desired angle. A surgeon may exert force in the direction of arrow 306 to achieve insertion of the spacer 102 in the direction of the major axis 304 in the intervertebral space. A surgeon may exert force in the direction opposite to arrow 306 to move the spacer 102 outwardly from the intervertebral space.

FIG. 3B depicts, for illustration purpose only, the external inserter 302 and the spacer 102 cut open in a plane parallel to and midway between the superior side 209 and the inferior side 211, exposing the internal cavity 201. A surgeon may alter the insertion angle of the spacer 102 during surgery in numerous and various positions to account for possible variations and conditions that might arise during surgery. Even though such angular adjustability is provided, the external inserter 302 and the spacer 102 remain fastened together during insertion and angular adjustment so that re-aligning the angle between one another, during or after an angular adjustment, may be easily accomplished without difficulty or unwanted separation.

FIG. 3C depicts the spacer 102 of FIG. 3B, rotated by about 90 degrees in the direction of arrow 308 with respect to the position depicted in FIG. 3B. The external inserter 302 is depicted as aligned with the minor axis 310 of the spacer 102. In certain configurations, the engaging mechanism of the spacer 102 (e.g., the post 252) is rotatable independent of the spacer 102 and the external inserter 302 may be rotated by simply using torque while the spacer 102 is firmly held in position such as in the intervertebral space (not shown in FIG.

3C). With the external inserter 302 resting against the resting surface 260 at the trailing end 208, a surgeon can exert both a rotational force to rotate the spacer and/or a translational force to move the spacer 102 back and forth along the major axis 304. It will be appreciated that the spacing between the resting surface 260 and the post 252 limits the maximum angle of rotation of the external inserter 302.

With reference to FIGS. 3A, 3B and 3C, during operation, a surgeon can direct the spacer 102 to a position within an intervertebral space by torsionally engaging the external inserter 302 with the post 252. Upon release of the torsional engagement between the external inserter 302 and the post 252, the spacer 102 can rotate within the intervertebral space around the post 252 freely to the extent permitted by the geometry of the trailing end 208. The clearance geometry of the trailing end 208 determines the amount of angulation the spacer 102 can go through within the intervertebral space. In certain embodiments, a surgeon can approach an intervertebral space and place the spacer 102 within the intervertebral space at a desired orientation and then disengage the spacer 102 from the external inserter 302, thereby allowing the spacer 102 to rotate within the intervertebral space without the need to change the orientation of the external inserter 302.

Figure 4:
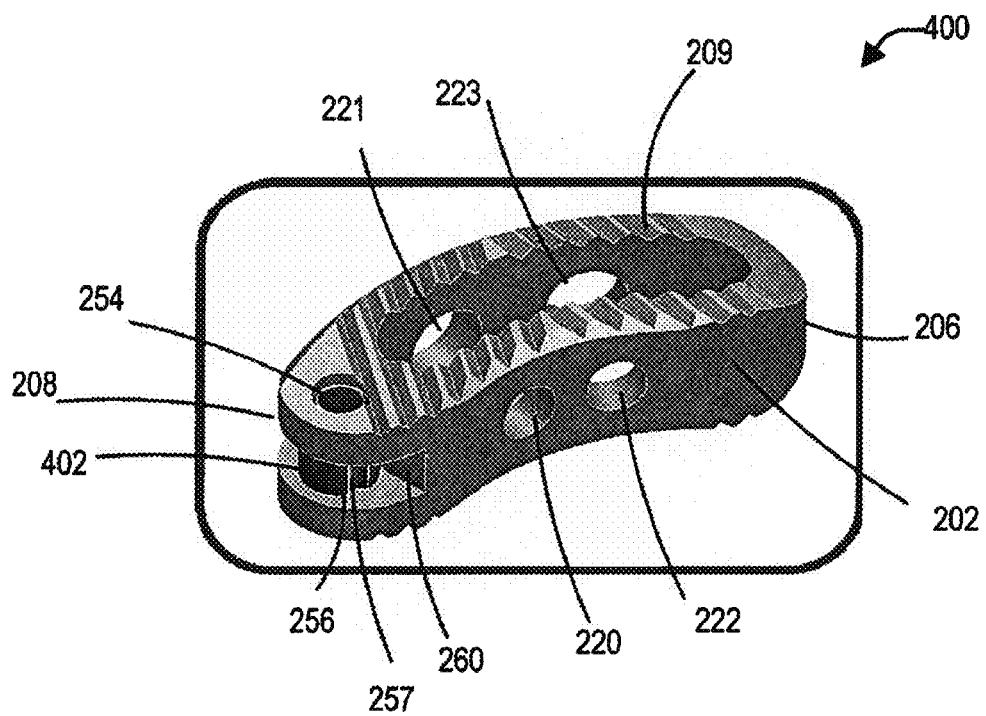
FIG. 4 is a diagrammatic view of an intervertebral spacer, in accordance with certain embodiments of the present application.

FIG. 4 depicts another embodiment 400 of the spacer 102 wherein the post 252 is covered by a sleeve 402. The sleeve 402 is configured to have matching features to couple firmly with the external inserter 302 (e.g., matching shape or matching groves). In certain embodiments, the sleeve 402 may be configured to freely rotate about the post 252. When the sleeve 402 is able to freely rotate, a surgeon is still able to move the spacer 102 using the external inserter 302 due to a frictional contact between the spacer 102 and the external inserter 302. In certain embodiments, the spacer 102 and the external inserter 302 are provided with complementary interlocking features (e.g., male/female connection) to establish a secure contact allowing movement of the spacer 102 by exertion of force from the external inserter 302. In certain embodiments, an interlocking feature, such as the groove 257, is provided on the sleeve 402 and a matching interlocking feature is provided on the external inserter 302 (not shown in FIG. 4) to establish a secure connection between the sleeve 402 and the external inserter 302. In certain embodiments, when the post 252 is not covered by the sleeve 402, an interlocking feature, such as the groove 257, is directly provided on the post 252.

Figure 5A:
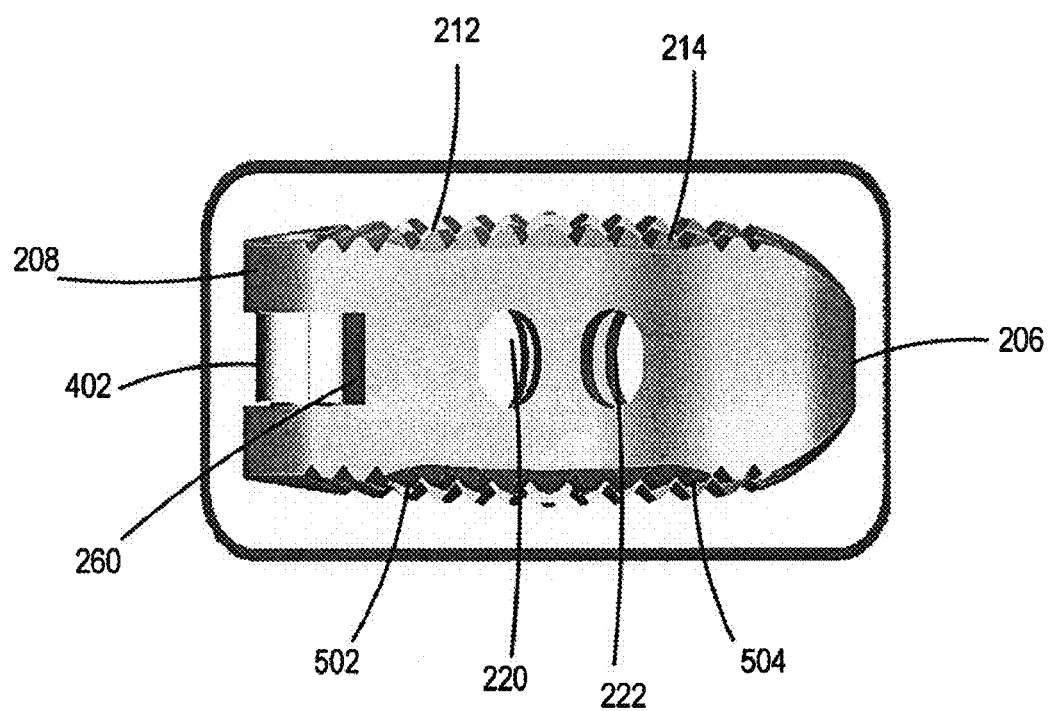
FIG. 5A is a posterior-side view of an intervertebral spacer, in accordance with certain embodiments of the present application.

FIG. 5A depicts a posterior side view of the spacer embodiment 400. In the depicted view, profiles of teeth 212, 214 are visible. The posterior side 202 has a smooth surface. The holes 220, 222 in the posterior side 202 are aligned with the holes 221, 223 in the anterior side 204, thereby allowing ready fusion of bone. The holes 220, 221, 222, 223 are depicted as elliptical, but may be of other shapes such as circular or multiple openings. Also, teeth 212, 214 have varying heights and widths in certain embodiments. In the depicted embodiment, the teeth towards the center of the spacer 102 are broader and less sharp compared to the teeth towards the trailing end 208 and the leading end 206.

Figure 5B:
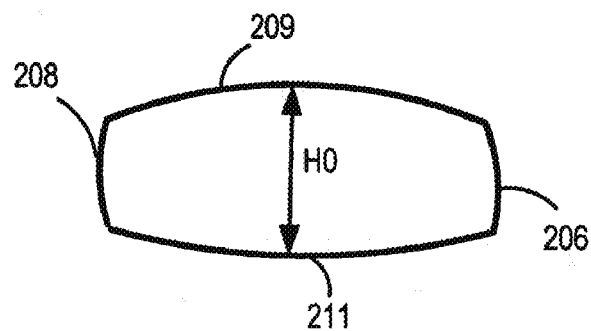
FIG. 5B is a posterior-side view of an intervertebral spacer, in accordance with certain embodiments of the present application.

Now referring to FIG. 5B, in certain embodiments, the superior side 209 and the inferior side 211 are shaped to be bulging at the center, depicted as height H0, with a slight taper, bringing the superior side 209 and the inferior side 211 closer to each other at the trailing end 208 and the leading end 206. Note that several details of the spacer 102 are omitted in FIG. 5B (e.g., post 252, teeth 212, 214) to depict the tapering feature with clarity. The slight taper is optional and may be useful in achieving a better fit in the intervertebral space by allowing a surgeon to better position the spacer 102 by sliding in a tapering end first.

Figure 5C:
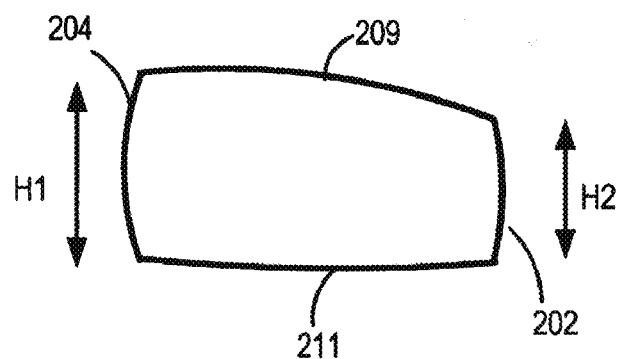
FIG. 5C is a trailing end side view of an intervertebral spacer, in accordance with certain embodiments of the present application.

Now referring to FIG. 5C, in certain embodiments, the height H1 of the anterior side 204 is greater than the height H2 of the posterior side 202 such that the superior side 209 slopes downwardly from the anterior side 204 to the posterior side 202. Note that several details of the spacer 102 are omitted in FIG. 5C (e.g., post 252, teeth 212, 214) to depict the height feature with clarity. The slight taper is optional and may be useful in achieving a better fit in the intervertebral space by allowing a surgeon to better position the spacer 102 by sliding in a tapering end first.

Figure 5D:
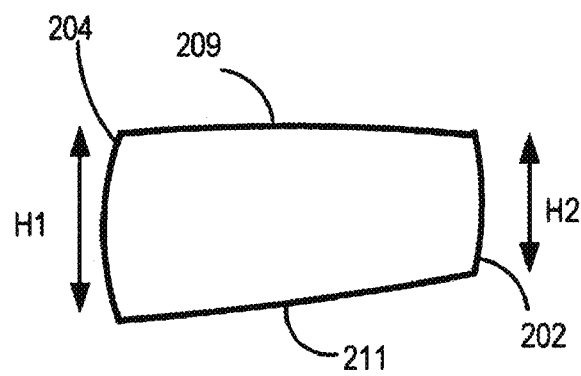
FIG. 5D is a trailing end side posterior-side view of an intervertebral spacer, in accordance with certain embodiments of the present application.

Now referring to FIG. 5D, in certain embodiments, the height H1 of the anterior side 204 is greater than the height H2 of the posterior side 202 such that the inferior side 211 slopes upwardly from the anterior side 204 to the posterior side 202. Note that several details of the spacer 102 are omitted in FIG. 5C (e.g., post 252, teeth 212, 214) to depict the height feature with clarity. The slight taper is optional and may be useful in achieving a better fit in the intervertebral space by allowing a surgeon to better position the spacer 102 by sliding in a tapering end first.

Figure 6:
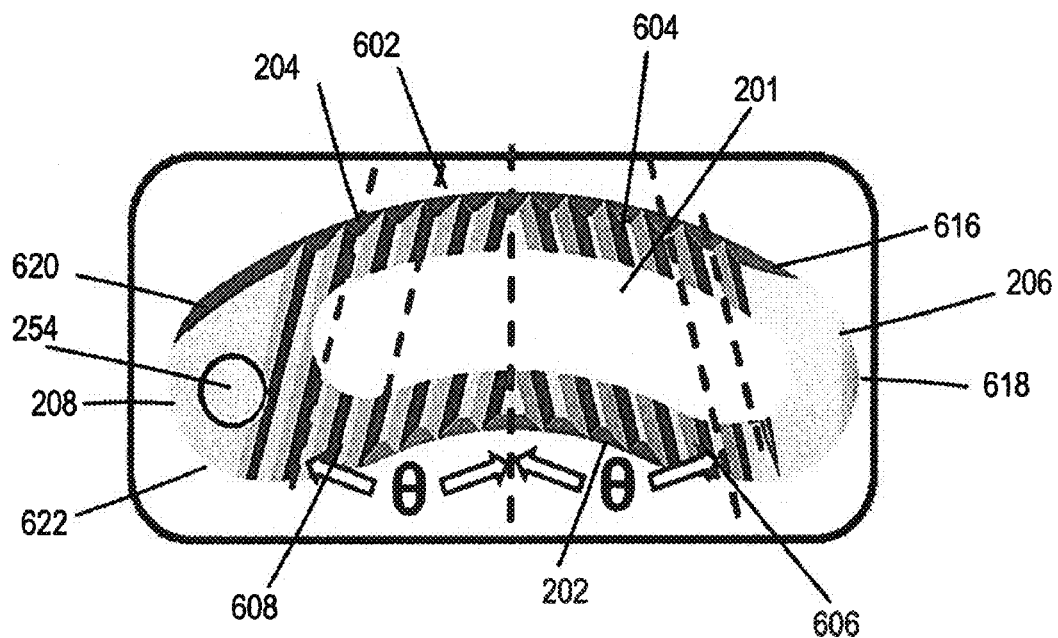
FIG. 6 is a superior-side view of an intervertebral spacer, in accordance with certain embodiments of the present application.

FIG. 6 depicts a view from the superior side 209. Teeth 212, 214 on the superior side 209 are arranged in two groups. In the first group 608 that is closer to the trailing end 208, the teeth are angled by θ degrees to point towards the leading end 206. In the second group 606 that is closer to the leading end 206, teeth are angled by θ degrees to point towards the trailing end 208. During insertion, when the spacer 102 is placed at the location of the insertion within an intervertebral space, the tooth pattern in group 606 aids rotation of the leading end 206 towards the concave side of the spacer 102 while the tooth pattern in group 608 on the trailing side 208 of the spacer 102 will aid rotation of towards the convex side of the spacer 102. In operation, the spacer 102 travels along a non-liner insertion path until its final position which is rotated from the initial position.

Still referring to FIG. 6, the leading end 206 comprises a generally arcuate portion 618 and a substantially straight portion 616 adjoining the arcuate portion 618. The arcuate portion 618 may be adjoining the posterior side 202, as depicted in FIG. 6, or the anterior side 204. In certain configurations, the trailing end 208 comprises a generally arcuate portion 622 and a substantially straight portion 620 adjoining the arcuate portion 618. Such shaping of the leading end 206 and the trailing end 208 aids the insertion and fitting of the spacer 102 into the intervertebral spacing.

Figure 7:
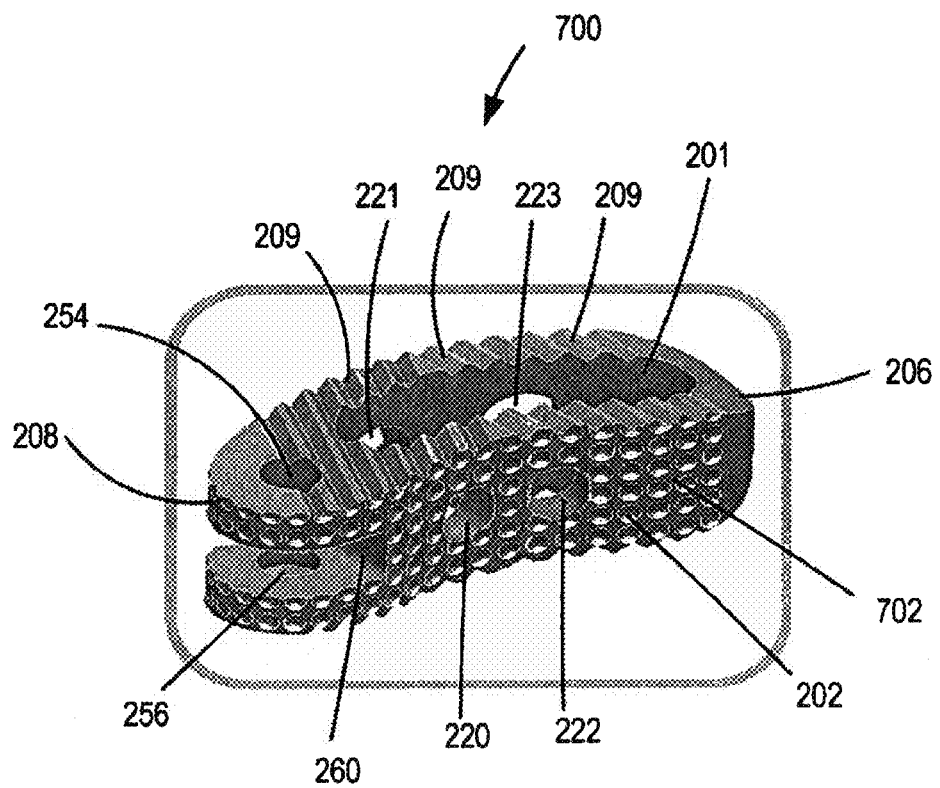
FIG. 7 is a diagrammatic view of an intervertebral spacer, in accordance with certain embodiments of the present application.

FIG. 7 depicts another embodiment 700 of the spacer 102, in a view similar to FIG. 2. No engaging mechanism is depicted (e.g., the post 252 or the sleeve 402) because the superior and the inferior recesses 254, 256 may be configured to accept either a post 252 or a post 252 with sleeve 402 around it. In the depicted embodiment, the spacer 102 includes interdigitation features 702 comprising an array of depressions for improved osseointegration. As the bone fusion mass is conducted around the spacer 102, the interdigitation features 702 provide additional mechanical interlocking of the bone to the spacer 102.

Figure 8:
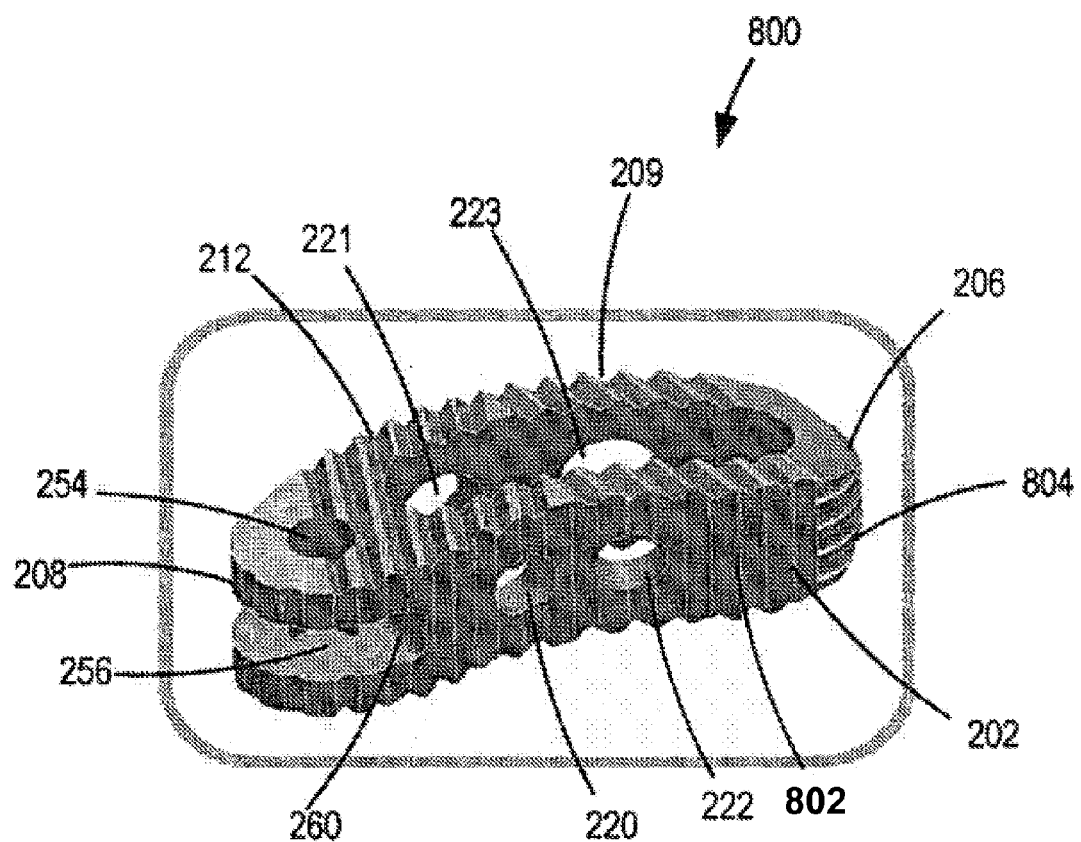
FIG. 8 is a diagrammatic view of an intervertebral spacer, in accordance with certain embodiments of the present application.

FIG. 8 depicts another exemplary embodiment 800 of spacer 102. No engaging mechanism is depicted (e.g., the post 252 or the sleeve 402) because the superior and the inferior recesses 254, 256 may be configured to accept either a post 252 or a post 252 with sleeve 402 around it. The depicted embodiment shows additional interdigitation features 802 that include wavy texture to the anterior and the posterior surfaces 204, 202. The interdigitation features 802 can also be used for ease of insertion in applications in which the spacer 102 needs to be turned around bony or tissue structures along the path of insertion. For example, in the embodiment depicted in FIG. 8, the interdigitation features 802 are in the form of vertical rails on the posterior side 202 provide resistance to forward movement aiding device rotation about the posterior side 202 while outer horizontal rails 804 circumscribe the convex perimeter of the leading end 106 to act as rails in which the spacer 102 may slide along the out annulus of the disc space, aiding insertion. Additionally the interior surfaces of the spacer 102 defining the internal cavity 201 may also have similar interdigitation features (not depicted in FIG. 8).

The description above discloses various embodiments of an interbody or intervertebral spacer 102. In certain embodiments, a post 252 is provided at the interface with the inserter 302 that enables the spacer 102 to rotate as being inserted into the disc space. A spacer 102 may be made from a biocompatible material such as titanium, cobalt chromium, tantalum, steel, and nitinol or polymers such as PEEK, PEEK reinforced, PEEK filled, and PCU.

In certain disclosed embodiments, an inserter 302 engages a sleeve 402 that can rotate freely about the interbody post 252. In certain configurations, the post 252 comprises a metallic biocompatible material such as titanium, cobalt chromium, tantalum, steel, and nitinol. In certain configurations, the post 252 comprises a biocompatible polymer such as PEEK, PEEK reinforced, PEEK filled, PCU and so forth. In certain aspects, the post 252 improves the mechanical strength of the spacer 102 by providing spacing support between opposite superior and inferior sides 209, 211. In certain embodiments, a metallic post 252 can be used as an X-ray marker for the spacer 102. The post 252 can be used as a hinge for a removal instrument.

According to certain embodiments, the spacer 102 includes inferior and superior patterned teeth 212, 214, 502, 504 to ease insertion. In certain embodiments, the spacer 102 comprises a pattern on the leading end 206 (e.g., teeth pattern or pattern 804), helping with rotation of the leading end 206 towards the implant's concave side. In certain embodiments, teeth 214, 504 closer to the leading end 206 are patterned at an angle from 0 to 90 degrees relative to the insertion path (the major axis 304 of the spacer 102) for a clockwise rotation of the spacer 102. In certain embodiments, the teeth 212, 502 closer to the trailing end 208, as depicted in FIG. 5, are patterned at an angle from 90 to 180 degrees relative to the insertion path for clockwise rotation of the spacer 102. In certain configurations, the outer surface teeth patterns 212, 214, 502, 504 are mirrored so that the spacer 102 rotates about the concave side in either a clockwise or counterclockwise direction depending on the insertion position or reference.

Another disclosed feature of a spacer 102 relates to interdigitation features for improved osseointegration or mechanical interlocking. The interdigitations may exist on the outer or inner surfaces to mechanically interlock external and internal bone formations. In certain embodiments, the interdigitation features has different patterns on the anterior and the posterior sides 202, 204. Certain embodiments of a spacer 102 include a coating with osseoconductive texture. The coating layer may be tailored to provide a surface energy suitable for bone cell attachment. In certain embodiments, the coating is deposited using chemical or physical deposition such as an Atomic Fusion Deposition process. In other embodiments, the coating is applied using a thermal spray such as titanium plasma spray or Hydroxyapatite (HA) plasma spray.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

Although embodiments of the present disclosure have been described and illustrated in detail, it is to be clearly understood that the same is by way of illustration and example only and is not to be taken by way of limitation, the scope of the present disclosure being limited only by the terms of the appended claims. Furthermore, one skilled in the art will recognize that while the present disclosure is generally described with reference to inventory management in a healthcare facility, certain configurations of the present disclosure may be used in inventory management systems used elsewhere.

What is claimed is:

1. An intervertebral spacer comprising: a leading end; a trailing end comprising an opening;
an arcuate anterior side connecting the leading end and the trailing end; an arcuate posterior side opposite to the arcuate anterior side and connecting the leading end and the trailing end; a superior side and an inferior side, and wherein the leading end extends continuously from the superior side to the inferior side; a major axis extending from the leading end to the trailing end of the spacer; a first interdigitation feature on an outside surface of the posterior side, the first interdigitation feature oriented lengthwise in a direction perpendicular to the major axis, wherein the first interdigitation feature comprises a first plurality of rails; and a second plurality of rails on an outside surface of the leading end, extending from the arcuate anterior side to the arcuate posterior side and lengthwise oriented in a direction perpendicular to that of the first plurality of rails.

2. The intervertebral spacer of claim 1, wherein the anterior side and the posterior side have different respective radii of curvature.

3. The intervertebral spacer of claim 1, wherein the anterior side, the posterior side, the leading end, and the trailing end form a cage having an internal cavity.

4. The intervertebral spacer of claim 1, further comprising a superior side, and wherein a first height of the anterior side is greater than a second height of the posterior side such that the superior side slopes downwardly from the anterior side to the posterior side.

5. The intervertebral spacer of claim 1, further comprising an inferior side, and wherein a first height of the anterior side is greater than a second height of the posterior side such that the inferior side slopes upwardly from the anterior side to the posterior side.

6. The intervertebral spacer of claim 1, wherein the first plurality of grooves covers the outside surface of the arcuate posterior side from the trailing end to a convex perimeter of the leading end.

7. The intervertebral spacer of claim 1, wherein the first plurality of grooves extends between the leading end and a midpoint that is located midway between the leading end and the trailing end.

8. The intervertebral spacer of claim 1, wherein the first interdigitation feature comprises an array of depressions oriented in a direction perpendicular to the major axis.

9. The intervertebral spacer of claim 1, wherein the anterior side and the posterior side define an internal cavity, and wherein the intervertebral spacer further comprises:

a second interdigitation feature on a side wall of the internal cavity.

10. The intervertebral spacer of claim 1, wherein the spacer is substantially rigid.

* * * * *